United States Patent [19]

Alphin et al.

[11] Patent Number: 4,717,563
[45] Date of Patent: Jan. 5, 1988

[54] 2-ALKOXY-N-(1-AZABICYCLO(2.2.2)OCT-3-YL) BENZAMIDES AND THIOBENZAMIDES IN A METHOD FOR ALLEVIATING EMESIS CAUSED BY NON-PLATINUM ANTICANCER DRUGS

[75] Inventors: Reevis S. Alphin; William L. Smith; Harry R. Munson, Jr.; Robert F. Boswell, all of Richmond, Va.

[73] Assignee: A. H. Robins Company, Inc., Richmond, Va.

[21] Appl. No.: 836,518

[22] Filed: Mar. 5, 1986

[51] Int. Cl.$^4$ .............................................. A61K 31/44
[52] U.S. Cl. ....................................... 424/10; 514/305
[58] Field of Search ........................................... 424/10

[56] References Cited
FOREIGN PATENT DOCUMENTS
99789A1 2/1984 European Pat. Off. ............ 514/305

*Primary Examiner*—Jerome D. Goldberg
*Attorney, Agent, or Firm*—D. E. Gillespie; I. Christoffel

[57] ABSTRACT

A method of controlling emesis caused by non-platinum anti-cancer drugs with 2-alkoxy-N-(1-azabicyclo[2.2.2]oct-3-yl)benzamides and thiobenzamides having the formula

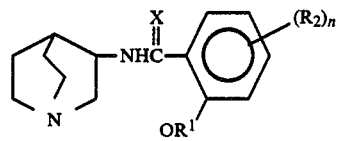

wherein X is oxygen or sulfur; $R_1$ is loweralkyl; and $R_2$ is selected from the group consisting of hydrogen, halo, 4,5-benzo, methylsulfonyl, loweralkoxy or Am and n is 1 or 2, and the pharmaceutically acceptable acid addition salts thereof is disclosed.

13 Claims, No Drawings

2-ALKOXY-N-(1-AZABICYCLO(2.2.2)OCT-3-YL) BENZAMIDES AND THIOBENZAMIDES IN A METHOD FOR ALLEVIATING EMESIS CAUSED BY NON-PLATINUM ANTICANCER DRUGS

BACKGROUND OF THE INVENTION

1. Field of Invention

The present invention relates to a method of controlling emesis caused by administration of non-platinum anti-cancer drugs to warm-blooded animals which utilizes certain N-(3-quinuclidinyl)benzamides and thiobenzamides; namely, the 2-alkoxy-N-(1-azabicyclo[2.2.2]oct-3-yl)benzamides.

2. Information Disclosure Statement

Certain compounds useful in the present invention and pharmaceutical compositions thereof were disclosed in U.S. application for patent Ser. No. 597,275 filed Apr. 6, 1984, and a continuation U.S. application for patent Ser. No. 788,190 filed Oct. 15, 1985, as having gastric emptying and anti-emetic properties, especially anti-emetic properties against emesis caused by administration of platinum-containing anti-cancer drugs.

Imbert, T. et al. in French Pat. No. 2,529,548 disclose that certain compounds useful in the present invention have gastric emptying properties; however, they do not disclose any anti-emetic properties exhibited by said compounds.

Quinuclidine analogs of sulpiride were prepared and studied by Mikhlina, E. E. et al. as reported in Khim-Farmatsevt, Zh. 10, No. 11, 56–60 (1976); C.A. 86: 155489r exemplified by the compound: 5-aminosulfonyl-N-(1-azabicyclo [2.2.2]oct-3-yl)-2-methoxybenzamide. This compound and others in the series were reported by the authors not to have anti-emetic activity. The above named compound was reported in USSR Pat. No. SU-414-261 to have neuroleptic activity. The compounds of the present invention show anti-emetic activity without neuroleptic activity (blockade of d-amphetamine lethality in mice).

Syntheses of 4-amino-N-(1-azabicyclo[2.2.2]oct-3-yl)benzamide and N-(1-azabicyclo[2.2.2]oct-3-yl)benzamide were reported by Mikhlina, E. E. et al. in Khim-Farmatsevt. Zh. 7, 20–24 (1974); C.A. 79: 146358a and the latter in Khim. Geterosikl. Soedin., Akad. Nauk. Latv. SSR 243–9 (1966); C.A. 65: 2220b. These compounds were reported to exhibit hypotensive, narcotic and ganglionic stimulation and blocking activities, properties not seen in the compounds of the present invention.

Synthesis of 4-amino-N-(1-azabicyclo[2.2.2]oct-3-yl)-3-chloro-5-trifluoromethylbenzamide was reported in Ger. Offen. No. 2,548,968; C.A. 87: 68001c and equivalently related U.S. Pat. No. 4,093,734 from 4-amino-3-chloro-5-trifluoromethylbenzoic acid chloride and 3-aminoquinuclidine. The compound is in a class among pyrrolidinyl and piperidinyl benzamides which are said to be useful as anxiolytics, anticonvulsives, antiemetics and antiulcerogenics. None of the compounds have orthoalkoxy substitution on benzamide as do the compounds of the present invention.

It is widely recognized that substituted benzamides are a class of drugs known to be effective in psychiatry [Sulpiride and Other Benzamides; International Workshop on Sulpiride and Other Benzamides, Florence, Feb. 17–18 (1978), Raven Press]. However, the 2-alkoxy-N-(1-azabicyclo[2.2.2]oct-3-yl)benazmides of this invention do not show neuropharmacological activity. This is in marked contrast to the compounds described in the prior art which show a range of pharmacological activities that include neuropharmacological effects.

SUMMARY OF THE INVENTION

The 2-alkoxy-N-(1-azabicyclo[2.2.2]oct-3-yl)benzamides and thiobenzamides of this invention have the formula:

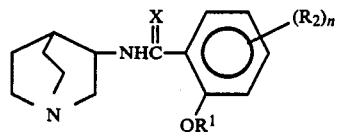

Formula I wherein X is oxygen or sulfur, $R_1$ is loweralkyl and $R_2$ is selected from the group consisting of hydrogen, halo, 4,5-benzo, methylsulfonyl, loweralkoxy or Am wherein Am is selected from amino, methylamino or dimethylamino, and n is 1 or 2, and the pharmaceutically acceptable acid addition salts thereof.

In the further definition of symbols in the formulas hereof and where they appear elsewhere throughout this specification and the claims, the terms have the following significance.

The term "loweralkyl" as used herein includes straight and branched chain radicals of up to eight carbons inclusive and is exemplified by such groups as methyl, ethyl, propyl, isopropyl, butyl, amyl, hexyl, heptyl, and octyl radicals and the like. The term "loweralkoxy" has the formula —O—loweralkyl.

The terms "halo" or "halogen" when referred to herein include fluorine, chlorine, bromine and iodine unless otherwise stated.

"Pharmaceutically acceptable acid addition salts" include the acid addition salts, hydrates, alcoholates and salts of the compounds of Formula I which are physiologically compatible in warm blooded animals. The acid addition salts may be formed by either strong or weak acids. Representative of strong acids are hydrochloric, sulfuric, and phosphoric acids. Representative of weak acids are fumaric, maleic, succinic, oxalic, citric, tartaric, cyclohexamic and the like.

Protected amino groups used in synthesis are acetylamino or benzoylamino radicals and the like on the benzamide moiety mentioned hereinbelow in synthetic methods.

Anti-emetic properties in the control of emesis due to administration of non-platinum anticancer drugs were determined by a modification of the method described by Gylys, J. A. in Res. Chem. Pathol. Pharmacol. 23, No. 1, Jan. 1979, pp 61–68. Test results show that compounds of Formula I are effective in controlling emesis associated with the following anticancer drugs: mechloroethamine hydrochloride (2-chloro-N-(2-chloroethyl)-N-methylethanamine hydrochloride), doxorubicin (adriamycin), dactinomycin (acetnomycin-D), and decarbazine. Test procedures are explained and results given hereinbelow in Examples 1–4. The compounds of Formula I can also be expected to control emesis caused by other anticancer drugs such as: cyclophosphamide (cytoxin), vincristine (leurocristine), procarbazine (N-(1-methylethyl)-4-[(2-methylhydrazino)methyl]benzamide), methotrexate and fluorouracil.

It is therefore a primary object to provide means for controlling violent emetic episodes due to the administration of non-platinum anticancer drugs.

DETAILED DESCRIPTION OF THE INVENTION

Preparation of Benzamides

The benzamido compounds of Formula I useful in the method of the invention are prepared by reacting a suitably activated benzoic acid derivative with 3-aminoquinuclidine to form the corresponding benzamide under a variety of conditions. Two general methods, A and B, are illustrated in the following equations:

Method A, using an Acid Chloride

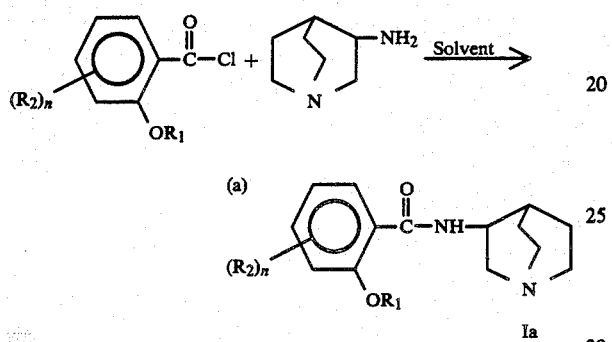

$R_1$, $R_2$ and n are as defined under Formula I except $R_2$ cannot be unprotected amino.
(a) Suitable solvents are chloroform, diethyl ether and tetrahydrofuran.
Method A is illustrated by Preparations 5, 6, 7, 9, 12 and 13.

Method B, using 1,1'-Carbonyldiimidazole

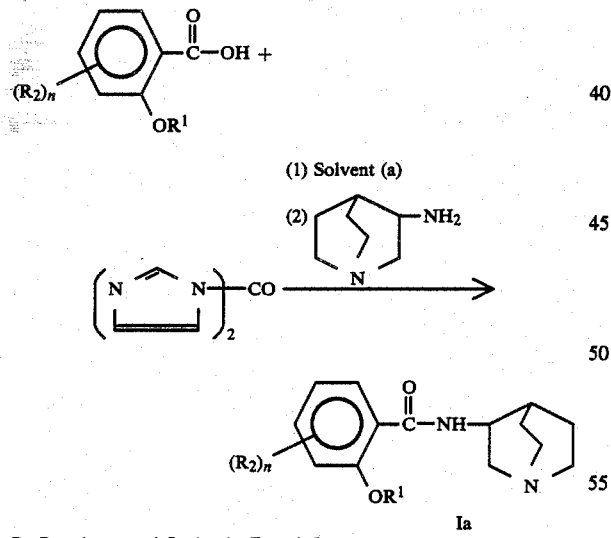

$R_1$, $R_2$ and n are as defined under Formula I.
(a) e.g., tetrahydrofuran.
Method B is illustrated by Preparations 1, 3, and 8.

Compounds wherein $R_2$ is primary amino may also be prepared from a compound prepared by Methods A or B, wherein $R_2$ is nitro by catalytic reduction of the nitro compound.

Alternatively, compounds wherein $R_2$ is amino may be prepared by procedures of Method A utilizing a starting benzoyl halide wherein the amino group has been protected, or they may be prepared from compounds prepared in Methods A or B wherein $R_2$ is nitro and reducing the nitro radical to an amino radical.

Preferably, the compounds wherein $R_2$ is amino or methylamino are prepared by Method B.

The free base of any compound of Formula I from its acid addition salt may be regenerated by usual procedures of partitioning between dilute aqueous base and a suitable solvent, separating the solvent layer, drying and evaporating.

Preparation of Thiobenzamides

The preparation of the thiobenzamido compounds of Formula Ib may be accomplished by mixing and reacting a benzamido compound of Formula Ia with a mixture of phosphorus pentasulfide ($P_2S_5$) and potassium sulfide ($K_2S$) or by mixing and reacting 3-aminoquinuclidine with an appropriately substituted benzaldehyde and sulfur. The reaction sequences are illustrated by the following:

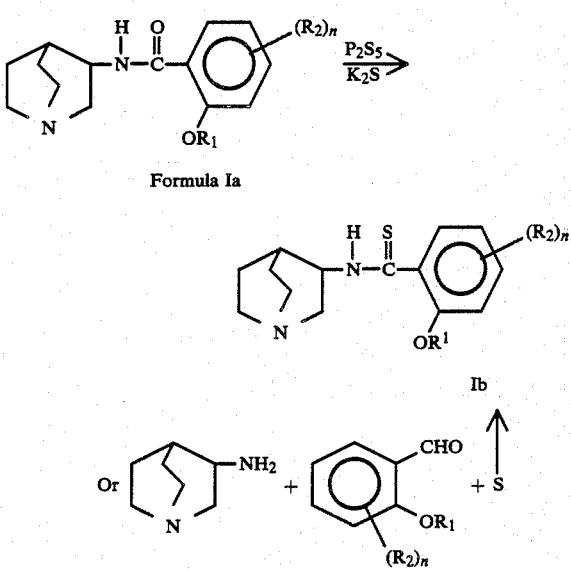

In these methods, compounds wherein $R_2$ is nitro may be reduced to compounds wherein $R_2$ is amino.

A preferred group of compounds encompassed by Formula I have the formula:

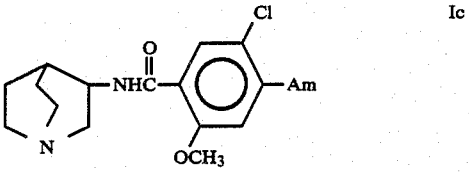

wherein Am is amino (i.e., —$NH_2$) or methylamino. The compounds are highly potent as anti-emetics in conjunction with treatment of cancer with non-platinum anticancer drugs and devoid of undesirable neuroleptic side effects even at much higher doses than required for aanti-emetic effects. As will be recognized from the above description, these compounds (Ic) are preferably prepared by Method B.

The following compound preparations 1–13 are provided merely by way of illustrating the methods of preparation and compounds and are not to be construed as being limiting in nature. The examples illustrate effectiveness of the compounds of Formula I in controlling emesis caused by non-platinum anticancer drugs.

Preparation 1

4-Amino-N-(1-azabicyclo[2.2.2]oct-3-yl)-5-chloro-2-methoxybenzamide, fumarate [1:1]

In a closed system equipped with an oil bubbler, 30 ml of tetrahydrofuran was added to a mixture of 4-amino-5-chloro-2-methoxybenzoic acid, 2.02 g, (0.010 mole) and 1,1'-carbonyldiimidazole, 1.62 g (0.010 mole) with stirring. When evolution of carbon dioxide ceased, nitrogen was bubbled through the reaction mixture for 1 hr. A solution of 3-aminoquinuclidine, 1.26 g, (0.010 mole) in 10 ml tetrahydrofuran was added dropwise to the stirred reaction mixture and stirring at room temperature continued for 3 hrs. TLC analysis (3% conc. ammonium hydroxide solution in methanol) showed some product formation. The mixture was heated at reflux temperature for 18 hours and then concentraded to an oil. TLC analysis showed the presence of the product, imidazole, and 3-aminoquinuclidine. The oil was dissolved in methylene chloride (75 ml) and washed twice with 50 ml portions of aqueous sodium bicarbonate solution. The methylene chloride layer was dried over anhydrous magnesium sulfate and concentrated to yield 2.0 g (67%) of a glassy amorphous solid, the free base of the title compound.

In another reaction on a 0.020 mole scale, 5.18 g (83.8%) of the product as the free base was obtained.

The products were combined, dissolved in methanol (20 ml) and the solution and treated with a solution of fumaric acid (2.73 g) in methanol (50 ml). Absolute ether was added to precipitate the salt which was collected by filtration and recrystallized from methanol-water (200:20) with isopropyl ether added to the point of incipient cloudiness. The recrystallized salt (5.38 g) melted at 223°–225° C.

Analysis: Calculated for $C_{19}H_{24}N_3O_6Cl$: C, 53.59; H, 5.68; N, 9.89. Found: C, 53.35; H, 5.72; N, 9.95.

Preparation 2

4-Amino-N-(1-azabicyclo[2.2.2]oct-3-yl)-5-chloro-2-methoxybenzamide, hydrochloride, hydrate [1:1:1]

To an isopropyl alcohol solution of the free base of the title compound such as was obtained by the procedure of Preparation 1, is added an equal molar amount of 37% (conc.) hydrochloric acid. The crude salt is separated by filtration and recrystallized from acetone-water to give the title compound, m.p. 158°–160° C.

Preparation 3

N-(1-Azabicyclo[2.2.2]oct-3-yl)-5-chloro-2-methoxy-4-methoxylaminobenzamide, fumarate [1:1]

To a mixture of 1,1'-carbonyldiimidazole, 1.23 g (0.00756 mole) and 5-chloro-2-methoxy-4-methylaminobenzoic acid, 1.63 g (0.00756 mole) was added 50 ml of tetrahydrofuran. Nitrogen was bubbled into the solution for 30 minutes to remove any carbon dioxide that was present. To the solution was added 3-aminoquinuclidine, 0.95 g, (0.00756 mole) in one portion, and the reaction mixture was stirred at ambient temperature for 16 hours. The reaction mixture was concentrated to an oil which was shown to be 1:1 mixture of the free base of the product and imidazole. The mixture was dissolved in 20 ml methanol and treated with a solution containing 0.47 g fumaric acid in 20 ml of hot methanol. Upon cooling, 1.52 g of white solid formed. Recrystallization from water-methanol gave 0.84 g of the product as a white solid, m.p. 237°–238° C.

Analysis: Calculated for $C_{20}H_{26}N_3O_6Cl$: C, 54.61; H, 5.96; N, 9.55. Found: C, 54.61; H, 5.98; N, 9.51.

Preparation 4

N-(1-Azabicyclo[2.2.2]oct-3-yl)-5-chloro-2-methoxy-4-(methylamino)benzamide, hydrochloride [1:1]

To an isopropyl alcohol solution of the free base of the title compound, such as was obtained by the procedure of Preparation 3, is added an equal molar amount of 37% (conc.) hydrochloric acid. The crude salt is separated by filtration and recrystallized from ethanol-water to give the title compound, m.p. 255°–258° C.

Preparation 5

N-(1-Azabicyclo[2.2.2]oct-3-yl)-2-methoxybenzamide, fumarate, hydrate [1:1:0.5]

In a closed system equipped with an oil bubbler, a solution of 2-methoxybenzoyl chloride, 2.76 g (0.0016 mole) in 50 ml absolute ether was added dropwise over 10 min to a stirred solution of 3-aminoquinuclidine, 1.81 g (0.0144 mole) in 100 ml absolute ether. After the addition was completed, the mixture was stirred at room temperature for an additional 2 hrs. The solid hydrochloride salt was collected by filtration under nitrogen. The salt (3.83 g) was dissolved in sodium bicarbonate solution and extracted twice with 25 ml portions of methylene chloride. The extract was dried over magnesium sulfate and concentrated to yield 1.25 g clear oil (33.3%). TLC analysis (3% conc. ammonium hydroxide in methanol) showed the free base to be pure. A solution of 1.17 g of the free base in 5 ml methanol was treated with a solution of 0.52 g fumaric acid in 10 ml methanol. Isopropyl ether was added to give approximately 100 ml of solution from which the fumarate salt precipitated. The salt was collected under nitrogen and dried in a vacuum oven at 60° C. overnight. NMR and elemental analyses showed that the product was a hemihydrate.

Analysis: Calculated for $C_{19}H_{25}N_2O_{6.5}$: C, 59.21; H, 6.54; N, 7.27. Found: C, 59.18; H, 6.30 N, 7.25.

Preparation 6

N-(1-Azabicyclo[2.2.2]oct-3-yl)-2,4-dimethoxybenzamide, hydrochloride [1:1]

A mixture of 3-aminoquinuclidine dihydrochloride, 6.95 g, (0.0349), 2,4-dimethoxybenzoyl chloride, 700 g, (0.0349 mole), anhydrous sodium carbonate, 36.99 g, (0.349 mole), 175 ml water, and 175 ml chloroform was stirred rapidly to achieve good mixing of the 2 layers for 20 hrs. The chloroform layer was then separated, washed with water, dried over anhydrous magnesium sulfate, and concentrated to an impure oil. The oil was triturated twice with 20 ml portions of petroleum ether to remove some impurities. The oil was then dissolved in ether and filtered to remove a small amount of insoluble material. The filtrate was treated with ethereal hydrogen chloride and the resulting salt collected to yield 2.70 g (23.7% yield) white solid. The salt was recrystallized from ethanol-isopropyl ether. Further recrystallization from methanol-ethyl ether yielded a white solid, m.p. 211°–212° C. The NMR analysis was satisfactory.

Analysis: Calculated for $C_{16}H_{23}N_2O_3Cl$: C, 58.80; H, 7.09; N, 8.57. Found: C, 58.38; H, 7.13; N, 8.44.

Preparation 7

N-(1-Azabicyclo[2.2.2]oct-3-yl)-2,4-dimethoxybenzamide, sulfate [1:1]

In a closed system equipped with an oil bubbler, a solution of 2,4-dimethoxybenzoyl chloride, 13.08 g, (0.0652 mole) in 200 ml absolute ether was dded dropwise over 30 minutes to a stirred solution of 3-aminoquinuclidine, 7.80 g, (0.0619 mole) in 200 ml absolute ether. The mixture was stirred overnight, and the solid hydrochloride salt of the product was filtered under nitrogen. The material was dried in a vacuum oven at 40° C. to give 18.70 g (92%). A 2.94 g (0.009 mole) portion of the hydrochloride salt in 20 ml methanol was treated with a solution of sodium methoxide prepared from 0.23 g (0.010 mole) sodium metal and 10 ml methanol. After standing a few minutes, the mixture was filtered and the filtrate concentrated on a rotary evaporator, and the residue was triturated with 75 ml methylene chloride. After filtering to remove some insoluble solids, the filtrate was concentrated to yield 2.53 g of the free base of the title compound (97% recovery from the hydrochloride salt). The free base was disssolved in 100 ml acetone and concentrated sulfuric acid (0.483 ml) added dropwise with stirring. The solid that formed was collected under nitrogen to give 2.76 g of the salt which recrystallized from mthanol-isopropyl ether and dried in a vacuum oven at 60° C. for 2 hrs and then overnight at 78° C., m.p. 223°–225° C.

Analysis: Calculated for $C_{16}H_{24}N_2O_7S$: C, 49.47; H, 6.23; N, 7.23. Found: C, 49.41; H, 6.30; N, 7.25.

Preparation 8

N-(1-Azabicyclo[2.2.2]oct-3-yl)-2,4-dimethoxybenzamide, fumarate [1:1.5]

In a closed system equipped with an oil bubbler, tetrahydrofuran, 100 ml, was added to a mixture of 2,4-dimethoxybenzoic acid, 3.64 g (0.020 mole) and 1,1'carbonyldimidazole, 3.24 g (0.020 mole). No evolution of carbon dioxide was observed and after stirring for 3 hrs, TLC (ethyl acetate) and mass spectral analysis showed that the starting material had reacted to form (2,4-dimethoxybenzoyl) imidazole and imidazole. A solution of 3-aminoquinuclidine, 2.52 g (0.020 mole) in 10 ml tetrahydrofuran was added to the mixture, and the solution was heated to reflux temperature for 1 hr and then allowed to stand overnight at room temperature. A solution of fumaric acid, 2.32 g (0.020 mole in 50 ml methanol was added to the reaction mixture. Tetrahydrofuran was added until the solution became slightly turbid. The solution was chilled in a refrigerator. The solid which precipitated from solution was collected by filtration and found to be a fumarate salt of 3-aminoquinuclidine. The filtrate was concentrated to an oil and triturated with tetrahydrofuran. The solid precipitate which formed on standing was filtered and shown by TLC (3% concentrated ammonium hydroxide in methanol) to be the desired product plus traces of imidazole and 3-aminoquinuclidine. Recrystallization from methanol-iropropyl ether gave 5.41 g white crystalline solid (67% yield calculated as the monofumarate). NMR and elemental analysis showed the salt to contain less than one equivalent of fumaric acid. The salt was dissolved in boiling methanol (50 ml) and treated with an additional 0.77 g (0.0066 mole) fumaric acid in 10 ml hot methanol. Isopropyl ether was added until the hot solution became turbid. The solid obtained on cooling was collected, recrystallized from methanol-isopropyl ether and dried in a vacuum oven at 78° C. overnight. NMR and elemental analysis showed the salt to be a 1.5 fumarate, m.p. 192°–192.5° C.

Analysis: Calculated for $C_{22}H_{28}N_2O_9$: C, 56.89; H, 6.08; N, 6.03. Found: C, 56.81; H, 6.13; N, 6.04.

Preparation 9

N-(1-Azabicyclo[2.2.2]oct-3-yl)-2-propoxybenzamide, hydrochloride [1:1]

To a solution of 3.82 g (0.0192 mole) of 3-amino quinuclidine dihydrochloride in about 25 ml of carbon dioxide-free water was added 8 g (0.025 mole) of barium hydroxide octahydrate. The mixture was warmed for 5 minutes and then dried to a powder on a rotary evaporator. While protecting from contamination with carbon dioxide in the atmosphere, the powder was extracted in sequence with hot benzene and a 1:1 mixture of benzene-methylene chloride solution. The combined extracts were dried over magnesium sulfate and the mixture filtered. To the filtrate with agitation was added dropwise a solution of 3.4 g (0.0171 mole) of 2-propoxybenzoyl chloride in 50 ml of methylene chloride. The mixture was warmed on a steam bath to evaporate about 75% of the methylene chloride. Ligroin (60–110) was added and the mixture solidified. The solid was recrystallized from anhydrous ethyl alcohol to give 3.9 g (62.0%), m.p. 210°–211° C.

Analysis: Calculated for $C_{17}H_{25}N_2O_2Cl$: C, 62.86; H, 7.75; N, 8.62. Found: C, 62.62; H, 7.59; N, 8.54.

Preparation 10

N-(1-Azabicyclo[2.2.2]oct-3-yl)-3-methoxy-2-naphthalenecarboxamide, hydrochloride [1:1]

A solution of 1.69 g (0.00768 mole) of 3-methoxy-2-naphthoic acid chloride in 15 ml of methylene chloride was added dropwise to a stirred solution of 0.97 g (0.00768 mole) of 3-aminoquinuclidine in 25 ml of methylene chloride in a closed system equipped with an oil bubbler. The reaction mixture was stirred overnight at ambient temperature, and then concentrated to give an off-white glassy solid. Two recrystallizations from methanol-isopropyl ether gave 1.95 g (73.4%) of the product as an off-white solid which was vacuum dried at ambient temperature, m.p. 248°–252° C.

Analysis: Calculated for $C_{19}H_{23}N_2O_2Cl$: C, 65.79; H, 6.68; N, 8.08. Found: C, 65.40; H, 6.72; N, 8.01.

Preparation 11

4-Amino-N-(1-azabicyclo[2.2.2]oct-3-yl)-5-chloro-2-methoxythiobenzamide, fumarate One half mole of 4-amino-N-(1-azabicyclo[2.2.2]oct-3-yl)-5-chloro-2-methoxybenzamide fumarate is partitioned between dilute sodium hydroxide and 400 ml of benzene. The benzene solution is dried with sodium sulfate and distilled to a volume of 250 ml. To this is added a finely-ground mixture of 9 g of phosphorous pentasulfide and 9 g of potassium sulfide. The mixture is refluxed for 4 hr. and an additional 9 g of phosphorous pentasulfide is added and reflux continued for 2 hr. The benzene is decanted off. The solid is dissolved in a suitable solvent and reacted with fumaric acid to give the title compound.

Preparation 12

N-(1-Azabicyclo[2.2.2]oct-3-yl)-2-methoxy-5-(methylsulfonyl)benzamide, hydrochloride [1:1]

A solution of 3-aminoquinuclidine (1.50 g, 0.0119 mole) in 20 ml tetrahydrofuran was added dropwise to a stirred solution of 2-methoxy-5-methanesulfonylbenzoyl chloride (2.95 g, 0.0119 mole) in 100 ml tetrahydrofuran. The mixture was stirred at ambient temperature for 20 hours, and filtered to yield 4.00 g (89.7%) of the product as the hydrochloride salt. The material was heated in 100 ml of boiling absolute ethanol and 50 ml methanol was added to give a clear solution. The solution was evaporated to a volume of 100 ml and cooled. The precipitate which formed was collected by filtration and vacuum dried at 110° C. for 8 hours, m.p. 219°–221° C.

Analysis: Calculated for $C_{16}H_{23}N_2O_4SCl$: C, 51.26; H, 6.18; N, 7.47. Found: C, 51.19; H, 6.26; N, 7.35.

Preparation 13

N-(1-Azabicyclo[2.2.2]oct-3-yl)-5-bromo-2,4-dimethoxybenzamide, hydrochloride [1:1]

A solution of 3-aminoquinuclidine (1.12 g, 0.0089 mole) in 20 ml tetrahydrofuran was added dropwise to a stirred solution of 5-bromo-2,4-dimethoxybenzoyl chloride (2.50 g, 0.0089 mole) in 100 ml tetrahydrofuran. The mixture was stirred at ambient temperature for 65 hours, and the solid was collected by filtration to yield 2.77 g. Recrystallization from methanol-isopropyl ether gave 1.45 g (40.2%), m.p. 240°–243° C.

Analysis: Calculated for $C_{16}H_{21}N_2O_3Br \cdot HCl$: C, 47.37; H, 5.47; N, 6.90. Found: C, 47.23; H, 5.62; N, 6.85.

EXAMPLE 1

Test on Emesis Caused By Dactinomycin (Actinomycin-D)

Tests on adult mongrel non-fasted dogs (of both sexes) were performed by first administering dactinomycin (150 mg/kg) intravenously followed after 60 minutes by a single dose of the compound of Preparation 2 (1.0 mg/kg) orally as a solution in a gelatin capsule. Test results showed the compound of Preparation 2 inhibited 50% of the emetic episodes in dogs when compared to the number of emetic episodes exhibited by dogs receiving the control (distilled water). Dogs were observed for 5 hr after the administration of dactinomycin and the number of emetic eposides recorded.

EXAMPLE 2

Test on Emesis Caused By Dacarbazine

Tests on adult mongrel non-fasted dogs (of both sexes) were performed by first administering dacarbazine (30 mg/kg) intravenously followed after 60 minutes by a single dose of the compound of Preparation 2 (1.0 mg/kg) orally as a solution in a gelatin capsule. Test results showed the compound of Preparation 2 inhibited 100% of the emetic episodes in dogs when compared to the number of emetic episodes exhibited by dogs receiving the control (distilled water). Dogs were observed for 5 hr after the administration of dacarbazine and the number of emetic episodes recorded.

EXAMPLE 3

Test on Emesis Caused By Doxorubicin (Adriamycin)

Test on adult mongrel non-fasted dogs (of both sexes) were performed by first administering the compound of Preparation 2 (1.0 mg/kg) orally followed 15 minutes later by the administration of doxorubicin (2 mg/kg) intravenously. Test results showed the compound of Preparation 2 inhibited 85.7% of the emetic episodes exhibited by dogs when compared to the number of emetic episodes exhibited by dogs receiving the control (distilled water). Dogs were observed for 2 hr after the administration of doxorubicin and the number of emetic episodes recorded.

EXAMPLE 4

Test on Emesis Caused By Mechlorethamine Hydrochloride (2-Chloro-N-(2-chloroethyl)-N-methylethanamine hydrochloride)

Test on adult mongrel non-fasted dogs (of both sexes) were performed by first administering mchlorethamine hydrochloride (0.4 mg/kg) intravenously followed after 60 minutes by the administration of the compound of Preparation 2 (1.0 mg/kg) orally as a solution in a gelatin capsule. Test results showed the compound of Preparation 2 inhibited 100% of the emetic episodes exhibited by dogs when compared to the number of episodes exhibited by dogs receiving the control (distilled water). Dogs were observed for 5 hr after the administration of mechlorethamine hydrochloride and the number of emetic episodes recorded.

Pharmaceutical Methods and Compositions

Generally, the method of controlling emesis associated with non-platinum anticancer drugs in accordance with this invention comprises administering internally to warm blooded animals including human beings certain 2-alkoxy-N-(1-azabicyclo[2.2.2]oct-3-yl)benzamides and thiobenzamides of Formula I, preferably Formula Ic, or a non-toxic organic or inorganic acid addition salt thereof in a wide variety of pharmaceutical forms well known in the art, preferably with a non-toxic pharmaceutical carrier such as is described below in an amount to control emesis associated with non-platinum anticancer drugs. The active agent is administered orally, subcutaneously, intravenously or intramuscularly or parenterally and, if necessary, in repeated doses until satisfactory response is obtained. The daily dosage is from about 5 to about 300 mg of active medication, advantageously from about 5 mg to 50 mg. Co-administration of the compounds of Formula I and non-platinum anticancer drugs is within the purview of the method of this invention.

In any particular method of controlling emesis due to administration of non-platinum anticancer drugs in cancer treatment, it may at times be desirable to administer a mixture comprised of compounds of Formula I, preferably Ic, and non-platinum anticancer drugs to the animal, including humans, the daily dosage being within the range cited above.

The pharmaceutical compositions, useful as antiemetics against emesis caused by non-platinum anticancer drugs, of this invention comprise at least one of the compounds of Formula I, preferably Formula Ic above, as active ingredients in an amount to provide effective antiemetic action against emesis caused by non-platinum anticancer drugs. The compositions contain 0.05 to 100 mg active medicament per unit dose. Preferably, the compositions contain from about 5 mg to 100 mg of medicament, advantageously from about 5 mg to about 50 mg per unit dose. The compounds are thus presented in a therapeutic composition suitable for oral, parenteral, subcutaneous, intramuscular, intraperitoneal or intravenous administration. Thus, for example, compositions for oral administration can take the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid; e.g., water or arachis oil contained in ampoules.

The pharmaceutical compositions for use in conjunction with administration of non-platinum anticancer drugs in cancer treatment will be formulated to contain from about 0.1 mg/kg to about 3.0 mg/kg body weight, preferably 1.0 mg/kg body weight or less. As stated above, co-formulation of non-platinum anticancer drugs and compounds of Formula I are within the scope of this invention and it is only necessary that the active ingredient of Formula I constitute an effective amount.

In all of the above, it is only necessary that a suitable effective dosage will be consistent with the dosage form employed. The exact individual dosages, as well as daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A method for treating warm blooded animals for emesis caused by administration of non-platinum anticancer drugs during cancer treatment which comprises internally administering thereto an emesis inhibiting effective amount of a compound selected from the group consisting of 2-alkoxy-N-(1-azabicyclo[2.2.2]oct-3-yl)benzamides and thiobenzamides of the formula:

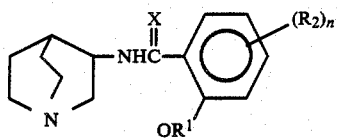

wherein;

X is oxygen or sulfur, $R_1$ is loweralkly containing up to eight carbon atoms, $R_2$ is selected from the group consisting of hydrogen, halo, 4,5-benzo, methylsulfonyl, loweralkoxy containing up to eight carbon atoms, or Am wherein Am is selected from amino, methylamino or dimethylamino, n is 1 or 2, and the pharmaceutically acceptable acid addition salts thereof.

2. The method of claim 1 wherein the compound is 4-amino-N-(1-azabicyclo[2.2.2]oct-3-yl)-5-chloro-2-methoxybenzamide or a pharmaceutically acceptable acid addition salt thereof.

3. The method of claim 1 wherein the compound is N-(1-azabicyclo[2.2.2]oct-3-yl)-5-chloro-2-methoxy-4-methylaminobenzamide or a pharmaceutically acceptable acid addition salt thereof.

4. The method of claim 1 wherein the compound is N-(1-azabicyclo[2.2.2]oct-3-yl)-2-methoxybenzamide or a pharmaceutically acceptable acid addition salt thereof.

5. The method of claim 1 wherein the compound is N-(1-azabicyclo[2.2.2]oct-3-yl)-2,4-dimethoxybenzamide or a pharmaceutically acceptable acid addition salt thereof.

6. The method of claim 1 wherein the compound is N-[1-azabicyclo[2.2.2]oct-3-yl]-2-propoxybenzamide or a pharmaceutically acceptable acid addition salt thereof.

7. The method of claim 1 wherein the compound is N-(1-azabicyclo[2.2.2]oct-3-yl)-3-methoxy-2-naphthalenecarboxamide or a pharmaceutically acceptable acid addition salt thereof.

8. The method of claim 1 wherein the compound is N-(1-azabicyclo[2.2.2]oct-3-yl)-2-methoxy-5-(methylsulfonyl)benzamide or a pharmaceutically acceptable acid addition salt thereof.

9. The method of claim 1 wherein the compound is N-(1-azabicyclo[2.2.2]oct-3-yl)-5-bromo-2,4-dimethoxybenzamide or a pharmaceutically acceptable acid addition salt thereof.

10. The method of claim 1 wherein said anti-cancer drug causing emesis is mechlorethamine hydrochloride.

11. The method of claim 1 wherein said anti-cancer drug causing emesis is dactinomycin.

12. The method of claim 1 wherein said anti-cancer drug causing emesis is adriamycin.

13. The method of claim 1 wherein said anti-cancer drug causing emesis is decarbazine.